United States Patent [19]

Bryson

[11] Patent Number: 4,927,582
[45] Date of Patent: May 22, 1990

[54] METHOD AND APPARATUS FOR CREATING A GRADUATED DISTRIBUTION OF GRANULE MATERIALS IN A FIBER MAT

[75] Inventor: Robert E. Bryson, Appleton, Wis.

[73] Assignee: Kimberly-Clark Corporation, Neenah, Wis.

[21] Appl. No.: 170,587

[22] Filed: Mar. 17, 1988

Related U.S. Application Data

[63] Continuation of Ser. No. 899,179, Aug. 22, 1986, abandoned.

[51] Int. Cl.[5] .......................... D04H 1/04; F15D 1/02; B65G 53/52
[52] U.S. Cl. ....................................... 264/113; 138/39; 138/45; 138/46; 264/40.7; 264/121; 264/518; 406/191; 425/81.1; 425/83.1
[58] Field of Search .............. 264/518, 113, 121, 40.7; 425/81.1, 83.1; 138/39, 45, 46, 92; 406/193, 191

[56] References Cited

U.S. PATENT DOCUMENTS

| 1,702,530 | 2/1929 | Williams . | |
|---|---|---|---|
| 2,646,381 | 7/1953 | Duvall | 264/121 |
| 3,025,202 | 3/1962 | Morgan et al. | 264/121 |
| 3,262,423 | 7/1966 | Willhite | 118/309 |
| 3,390,702 | 7/1968 | Gilmont | 138/45 |
| 3,670,731 | 6/1972 | Harmon | 128/284 |
| 3,888,257 | 6/1975 | Cook et al. | 128/296 |
| 3,973,291 | 8/1976 | Kolbach | 19/148 |
| 4,087,506 | 5/1978 | Cook et al. | 264/112 |
| 4,212,302 | 7/1980 | Karami | 128/287 |
| 4,264,289 | 4/1981 | Day | 425/83.1 |
| 4,333,462 | 6/1982 | Holtman et al. | 128/287 |
| 4,356,997 | 11/1982 | Beffano | 251/214 |
| 4,388,056 | 6/1983 | Lee et al. | 425/83.1 |
| 4,540,454 | 9/1985 | Pieniak et al. | 156/62.2 |
| 4,619,562 | 10/1986 | Brännström | 406/182 |

FOREIGN PATENT DOCUMENTS

| 0159630 | 10/1985 | European Pat. Off. . |
| 0160572 | 11/1985 | European Pat. Off. . |
| 56-89839 | 7/1981 | Japan . |
| 2175024 | 11/1986 | United Kingdom . |

OTHER PUBLICATIONS

Technical Bulletin, "SAP Sheet", Sanyo Chemical Industries, dated 10/82.

Primary Examiner—Jan H. Silbaugh
Assistant Examiner—Mary Lynn Fertig
Attorney, Agent, or Firm—Paul Yee

[57] ABSTRACT

A distinctive apparatus for forming an absorbent body includes a forming chamber, and a fiber delivering mechanism for providing a flow of fibrous material within the forming chamber. A forming layer, which is located in the forming chamber and is movable therein, receives deposit of the fibrous material thereon. A conduit mechanism supplied a flow of dispersed bodies of high-absorbency material, which enter the forming chambers and intermix with the flow of fibrous material thereon. A regulating mechanism controls a velocity of the flow of high-absorbency material into the flow of fibrous material to thereby form a selected distribution of high-absorbency material within the fibrous material deposited onto the forming layer.

25 Claims, 4 Drawing Sheets

METHOD AND APPARATUS FOR CREATING A GRADUATED DISTRIBUTION OF GRANULE MATERIALS IN A FIBER MAT

This is a continuation of co-pending application Ser. No. 899,179 filed on Aug. 22, 1986, now abandoned.

FIELD OF THE INVENTION

The present invention relates to a method and apparatus for producing an absorbent body containing granules or particles of high-absorbency material therein. More particularly, the present invention relates to a method and apparatus for producing selected concentration distributions and gradients of high-absorbency materials within the absorbent body.

BACKGROUND OF THE INVENTION

High-absorbency materials may be organic or inorganic, and can include, for example, clays, pectin, peat moss, carboxymethylcellulose, hydrophilic polymers and mixtures thereof. Such materials have been included into fibrous absorbent bodies to increase the absorbent capacity. The absorbent bodies have then been incorporated into various articles, such as bandages, diapers, feminine sanitary pads, incontinence garments, and the like.

Typically, the absorbent body is composed of cellulose wadding or cellulosic wood pulp material commonly referred to as "fluff". An absorbent body composed of wood pulp fluff is typically formed by employing conventional airlaying techniques, such as those shown in U.S. Pat. No. 4,388,056 issued June 14, 1983 to F. Lee, et al. and U.S. Pat. No. 3,973,291 issued Aug. 10, 1976 to C. Kolbach.

The high-absorbency material has been incorporated into the absorbent body employing various arrangements. For example, the high-absorbency material has been confined to selected layers or pockets within the absorbent body, as representatively shown in U.S. Pat. No. 1,702,530 issued Feb. 19, 1929 to H. Williams and U.S. Pat. No. 4,333,462 issued June 8, 1982 to D. Holtman, et al. The high-absorbency material has also been configured as particles distributed into an absorbent body, as shown in U.S. Pat. No. 3,670,731 issued June 20, 1972 to C. Harmon. Other absorbent body configurations have restricted the high-absorbency material to a rectilinear, central zone of the absorbent body, thereby leaving lateral zones that are free of the high-absorbency material. For example, see U.S. Pat. No. 3,888,257 issued June 10, 1975 to R. Cook, et al. Still other configurations have restricted the high-absorbency material to the lateral zones of the absorbent body, as representatively shown in U.S. Pat. No. 4,212,302 issued July 15, 1980 to H. Karami.

To distribute and locate the high-absorbency material within the absorbent body, various techniques have been employed. For example, the high-absorbency material has been secured to a carrier layer or web which is then assembled into the absorbent body. A typical configuration is shown in European patent application EP 0 160 572 A2 published Nov. 6, 1985 with the inventors listed as E. Erdman, et al. Particles of high-absorbency material have also been deposited onto a fluff pad and distributed into the voids between the absorbent fibers employing high velocity air to inject particles into the fluff pad. For example, see U.S. Pat. No. 4,087,506 issued May 2, 1978 to R. Cook, et al. Still other devices, such as the apparatus described in U.S. Pat. No. 3,262,423 issued July 26, 1966 to W. Willhite, have been employed to uniformly deposit a particulate material onto a moving porous web.

Conventional devices and techniques, such as those discussed above, have not, however, been sufficiently capable of efficiently producing an absorbent body having high-absorbency material distributed in selected concentration distributions or gradients through the thickness dimension or across the width dimension of the absorbent body. In addition, the conventional forming techniques have not been sufficiently able to deliver high-absorbency materials in a substantially uniformly dispersed configuration that can be readily directed and distributed into predetermined locations and patterns within the absorbent body. As a result, articles, such as disposable diapers, feminine sanitary napkins, incontinence garments and the like, have not been able to efficiently incorporate desired distribution patterns of components to more effectively use the absorbent capacities of the high-absorbency material.

BRIEF DESCRIPTION OF THE INVENTION

The present invention provides a distinctive method and apparatus for forming an absorbent body having selected patterns of high-absorbency material distributed therein. Generally stated, the apparatus includes a forming chamber, and a fiber delivering means for providing a flow of fibrous material within the forming chamber. A forming layer, which is located in the forming chamber and is moveable therein, receives a deposit of the fibrous material thereon. Conduit means supply a flow of dispersed bodies of high-absorbency material which enters the forming chamber and intermixes with the flow of fibrous material therein. Regulating means control a flow velocity of the high-absorbency material into the flow of fibrous material to thereby form a selected distribution of high-absorbency material within the fibrous material deposited onto the forming layer.

The present invention further provides a method for forming an absorbent body. The method includes the steps of providing a flow of fibrous material within a forming chamber, and receiving a deposit of the fibrous material on a forming layer, which is located in the forming chamber and is moveable therein. A flow of dispersed bodies of high-absorbency material enters the forming chamber and intermixes with the flow of fibrous material therein. A flow velocity of the high-absorbency material into the flow of fibrous material is controlled to thereby form a selected distribution of high-absorbency material within the fibrous material deposited onto the forming layer.

The present invention can advantageously provide a method and apparatus which can more efficiently and more reliably distribute high-absorbency materials into selected locations and patterns within an absorbent body, such as a pad or web comprising cellulosic fibers. In particular, the present invention can more effectively deliver a substantially uniformly dispersed configuration of high-absorbency bodies transported by a gaseous stream into a forming zone. In addition, the invention can more reliably distribute the high-absorbency material into desired patterns, such as selected concentration gradients, within the absorbent body.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The present invention can be employed to produce selected mixtures and distributions of one type of fibrous or particulate material into a second type of filamentary or fibrous material during an airlaying or airforming operation. The particular embodiment of the invention set forth in the following detailed description of the invention relates to distributing particles of relatively high-absorbency material into a pad of cellulosic fluff. However, other mixtures of materials may be produced employing the present invention, depending on the particular parameters desired in the absorbent body. For example, specific distributions of hydrophilic and hydrophobic materials may be desired to provide selected wicking characteristics within the absorbent body. Such alternative configurations and uses are contemplated as being within the scope of the present invention.

Figure 1:
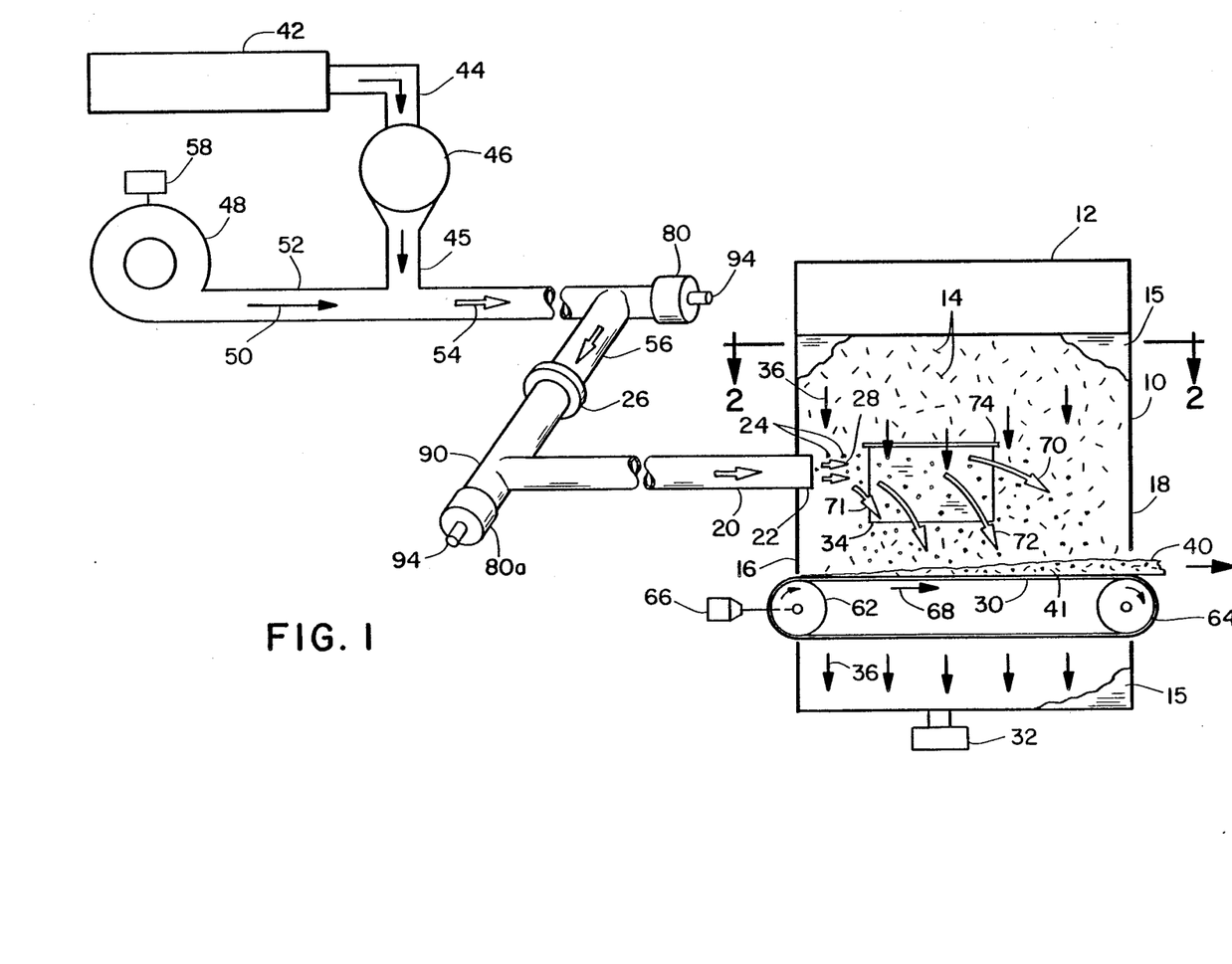
FIG. 1 shows a schematic view of a representative apparatus of the invention.
Figure 2:
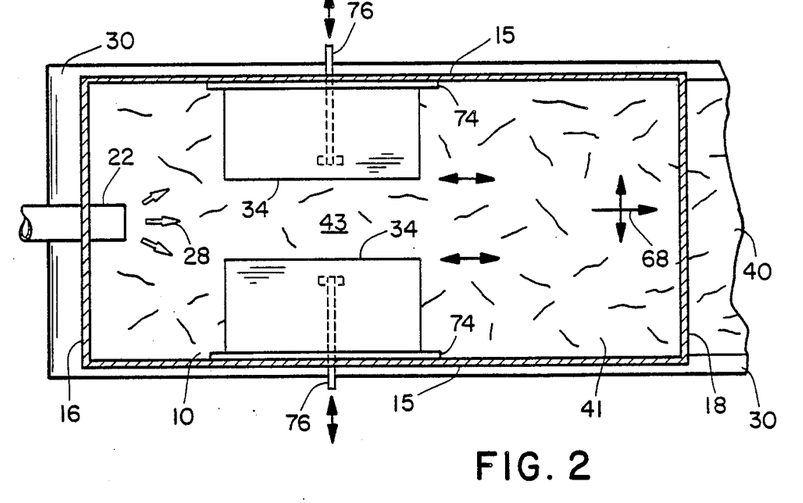
FIG. 2 shows a cross-sectional, top plan view of the forming chamber taken along line 2—2 of FIG. 1.

Referring now to FIGS. 1 and 2, a representative apparatus of the invention includes a forming chamber 10 and a fiber delivery means, such as fiberizer 12, for providing a flow of fibrous material 14 within the forming chamber. A forming layer 30, which is located in forming chamber 10 and is moveable therein, receives a deposit of fibrous material 14 thereon. Conduit means, such as pipeline 20 and one or more nozzles 22, supply of flow of dispersed bodies of high-absorbency material 24. This flow of high-absorbency material enters forming chamber 10 and intermixes with the flow of fibrous material 14 therein. Regulating means, such as flow angle adjuster 26, controls a flow velocity 28 of the high-absorbency material 24 within the fibrous material 14 deposited onto forming layer 30 to form web 41.

Forming chamber 10 includes sidewalls 15 and endwalls which are constructed and arranged to define a generally enclosed volume. Endwalls 16 and 18 have suitable entrance and exit openings formed therethrough to allow the entry of forming layer 30 and the removal of airlaid absorbent body 40 from the forming chamber.

Fiberizer 12 may comprise any one of a number of types of fiberizing devices, such as conventional hammermills. Sheets of selected fibrous material are typically fed into fiberizer 12, and are disintegrated into a plurality of individual fibers 14 which are ejected or otherwise introduced into chamber 10.

Fibers 14 are typically composed of absorbent, wood pulp fibers commonly referred to as fluff. The fibers may also be composed of staple fibers, polymeric fibers, cellulosic fibers and mixtures thereof, as well as mixtures of absorbent fibers with generally hydrophobic fibers.

The forming apparatus of the invention may further include vacuum means 32, such as a conventional blower mechanism, for creating a selected pressure differential through forming chamber 10 and past forming layer 30. The vacuum means is typically located underneath forming layer 30 to create an airflow through chamber 10 which is generally directed from fiberizer 12 and past forming layer 30. This air flow helps to direct and control the deposit of fibers 14 and particles 24 onto the forming layer.

Forming layer 30, for example, comprises a foraminous forming screen configured as an endless belt which moves about support rollers 62 and 64. A suitable driving means, such as electric motor 66, is operably connected to move forming layer 30 through chamber 10 at a selected speed along movement direction 68. Fibers 14 and high-absorbency particles 24 deposit onto the portion of forming layer 30 within forming chamber 10 to form a web 41, which eventually develops into absorbent body 40. Since forming layer 40 moves generally from endwall 16 toward the exit opening through endwall 18, the depth or thickness of web 41 on any particular section of forming layer 30 gradually increases as that forming layer section traverses through the forming chamber. The fiber deposition rate onto forming layer 30 and the movement speed of the forming layer can be suitably adjusted to control the finally formed thickness of the airlaid fibrous web 41.

Figure 3:
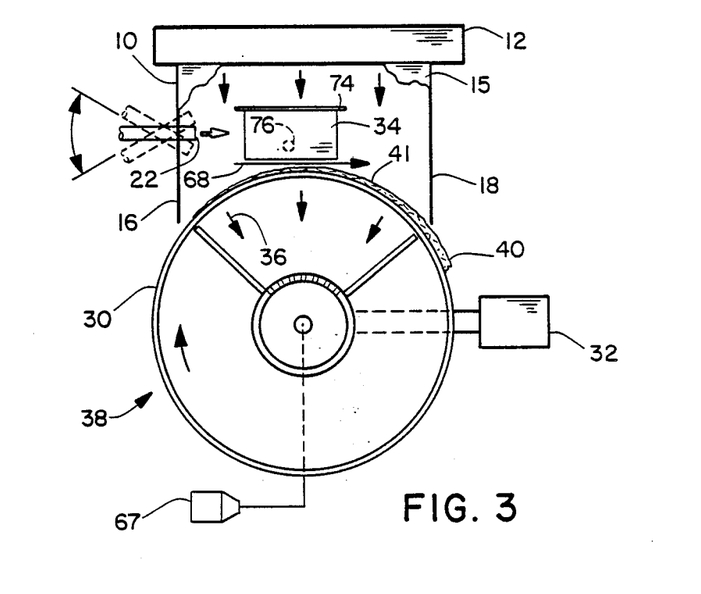
FIG. 3 representatively shows an embodiment of the invention which employs a drum former device.
Figure 4:
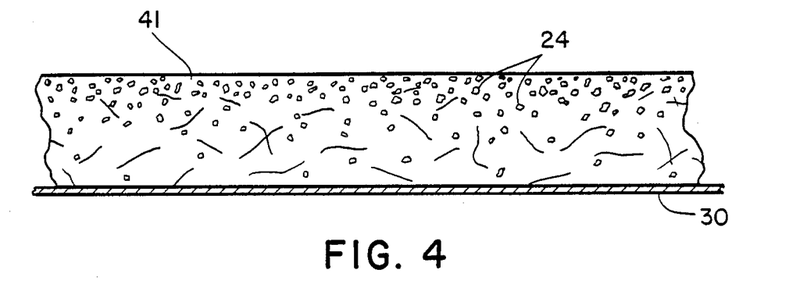
FIGS. 4 and 4a representatively show cross-sectional, elevational views of absorbent pads which include a concentration gradient of high-absorbency material through the thickness of the pad.
Figure 4A:
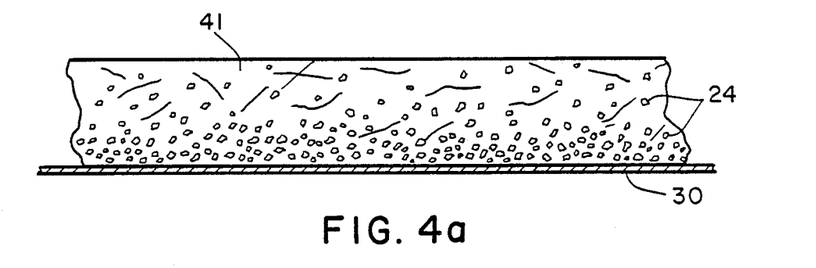

In another aspect of the invention, forming layer 30 comprises a foraminous forming screen carrier on an outer circumferential surface of a rotatable drum 38, as representatively shown in FIG. 3. A suitable drive means, such as motor 67, rotatably activates drum 38 to move forming layer 30 through forming chamber 10.

To increase the absorbent capacity of absorbent body 40, it has been desirable to add quantities of relatively high-absorbency material to the fibers comprising the absorbent body. Such high-absorbency materials are capable of holding, on a weight basis, at least about 15 parts of water per part of high-absorbency material. Preferably, the high-absorbency material is capable of holding at least about 50 parts of water per part of high-absorbency material, and more preferably is capable of holding at least about 70 parts of water per part of high-absorbency material. Examples of suitable high-absorbency materials include inorganic materials, such as clays, natural organic materials, such as agar gum and pectin, and synthetic hydrophilic polymers, such as sodium polyacrylate or polyacrylanitrile polymers. Various combinations of mixtures of such high-absorbency materials may also be employed.

With the shown embodiment of the invention, high-absorbency material is supplied from storage means 42 through transport conduit 44 into a metering device 46. The metering device delivers a desired flow rate of individual, particulate-type bodies of high-absorbency material into a gaseous flow transport system by way of supply conduit 45.

Figure 5:
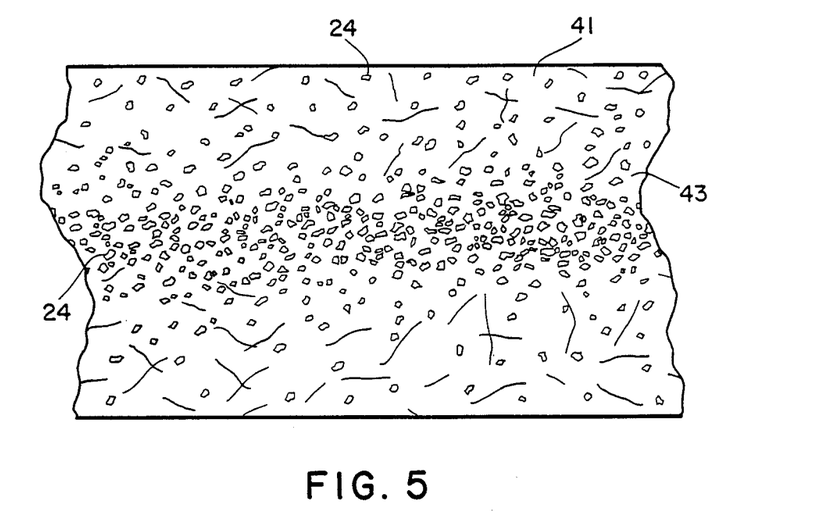
FIG. 5 representatively shows a cross-sectional, top view of an absorbent pad which includes a concentration gradient of high-absorbency material along the cross-direction of the pad.

Gas delivery means, such as blower 48, provides a selected volume rate of gas flow 50 into gas conduit 52. Gas flow 50 mixes with the high-absorbency particles to produce an essentially dilute suspension or dispersion 54 of high-absorbency material within the gas flow. The dilute dispersion is, on a volume basis, composed of at least about 80% gas, and preferably is composed of at least about 95% gas. Gas flow 50, among other things, transports the resultant, high-absorbency material dispersion 54 to forming chamber 10 through a suitable conduit system, such as transport pipeline 56. Where transport pipeline 56 must be configured to accommodate turns and bends in the transport path, fluid conduit sections, such as fittings comprising blinded T-bends 80, are incorporated into the transporting system to provide desired changes in direction.

The bodies of high-absorbency material employed to form dispersion 54 are typically particles which may have regular shapes or irregular shapes, such as elongated forms The particles typically measure about 50–1000 micrometers in size, preferably measure about 100–800 micrometers and more preferably measure about 200–600 micrometers in size to provide improved processability through the apparatus of the invention.

Pipeline 20 directs the gas/particle dispersion 54 through nozzle 22 into forming chamber 10. The illustrated embodiment of the invention includes a single nozzle 22 which, for example, may comprise a conduit of circular cross-section measuring about 5 cm. in diameter. If desired, other regular or irregular nozzle shapes or sizes may be employed. The nozzle may protrude into chamber 10, if desired, to adjust the distribution of high absorbency particles through the thickness of web 41. A larger amount of protrusion can reduce the amount of particles deposited near the forming layer side of web 41.

Depending on the size and weight of the individual particles of high-absorbency material, the dispersed particles will tend to follow various trajectories 70-72 to intermix with the flow of fibers 14 moving through chamber 10 toward forming layer 30. Some of the particles will follow a shorter trajectory 71 to deposit high-absorbency material into web 41 at locations nearer endwall 16. Other particles will follow longer trajectories 70 to deposit into web 41 at locations closer to endwall 18. The remainder of particles will follow intermediate trajectories 72 to deposit into web 41 at more centrally located, intermediate regions between endwalls 16 and 18. Since web 41 is gradually increasing in thickness as it traverses through chamber 10, particles 24 can be selectively distributed through the thickness dimension of web 41 to produce a desired concentration gradient therein.

To produce desired distribution patterns and gradients through the web thickness, an initial flow velocity 28 of the particle dispersion into chamber 10 is selectively regulated by adjusting the angular direction of the flow, the height of nozzle 22 above forming layer 30, and the speed of the flow. Blower control 58 in the shown embodiment, adjusts the volume rate of gas flow into the system, and as a result, can adjust the magnitude of the velocity; i.e. speed; of the gas/particle flow. For example, in one embodiment of the invention, blower 48 is adjusted to produce a flow speed of the high-absorbency material dispersion which measures at least about 15 m/sec. If the flow speed is increased, relatively more high-absorbency material can be deposited toward the upper, free surface side of web 41, as illustrated in FIG. 4. If the flow speed is decreased, relatively more high-absorbency material can be deposited toward the forming layer side of web 41, as illustrated in FIG. 4a. In a particular aspect of the invention, the flow speed is within the range of about 15–45 m/sec.

The initial direction of the initial dispersion flow 28 into chamber 10 can be selectively changed employing angle adjusting mechanism 26, which is operated to change the angular orientation of nozzle 22. In a particular, preferred aspect of the invention, angle adjusting mechanism 26 comprises a rotatable connection between the transport pipeline 56 and the entrance arm of the last blinded-T fitting 80a located prior to the entrance of the particle dispersion into chamber 10. Locating the pivot mechanism proximate to, and preferably immediately before, the change in direction effected by blinded-T fitting 80a helps to ensure that a desired, substantially uniform distribution of high-absorbency particles is maintained over the cross-section of the transport gas flow through pipeline 20 and out of nozzle 22. If any angle adjusting mechanism is located downstream from fitting 80a, undesired variations or concentrations of the particle distribution may be created within pipeline 20. In the embodiment shown in FIG. 1, nozzle 22 is oriented generally parallel to the movement direction 68 of forming layer 30. As a result, nozzle 22 directs particles 24 along an initial direction which is generally parallel to the local horizontal.

Nozzle 22 can also be suitably adjusted to a nonparallel angle slanted toward or away from forming layer 30. If the nozzle is angled toward the forming layer, relatively more high-absorbency material can be deposited nearer the forming-layer side of web 41. If the nozzle is angled away from forming layer 30, relatively more high-absorbency material can be deposited nearer the upper, free surface side of web 41. For example, in a particular aspect of the invention, nozzle 22 is constructed and arranged to be pivotable plus or minus 45 degrees relative to a plane positioned generally parallel to the forming layer, and preferably is pivotable plus or minus 10 degrees relative to such plane, to angle nozzle 22, respectively, away or toward the forming layer.

A further aspect of the invention includes an arrangement of baffle members 34, which can be employed to regulate the cross-directional distribution of high-absorbency materials across the width of web 41. Referring to FIG. 2, representative baffle members 34 are located within chamber 10 and are selectively positionable therein. The major surfaces of the baffle members are generally vertically disposed, and are substantially aligned along the movement direction 68 of the forming layer. In the shown embodiment, a pair of baffle members is positioned one on each side of nozzle 22 with the two baffle members spaced apart by a selected distance.

Baffles 34 are connected to rotate about pivot members 74, which are connected to the upper, top edges of the baffles and to chamber walls 15. A movement of adjustment arms 76, as indicated by the associated arrows, controls the slant of baffles 34 and thereby effectively controls the spacing between the baffles.

Various parameters associated with baffle members 34 can be adjusted to obtain desired cross-directional distributions of high-absorbency particles within web 41. Such parameters include the spacing between the baffle members, the length dimensions of the baffle members and the particular position of the baffle members along the machine direction of chamber 10, as defined by the movement direction 68 of forming layer 30. More particularly, a closer spacing of baffle members 34 can increase the relative amount of particles deposited on a central, medial portion of web 41, as compared to the particle amount deposited on the lateral edge of web 41. Conversely, a greater spacing between baffle members 34 can create a more uniform distribution of particles across the width of web 41. For a selected spacing between the baffle members, a positioning of the baffles closer to nozzle 22 can reduce the high-absorbency material concentration at the lateral side edges of web 41 relative to the central region of the web, as representatively shown in FIG. 5. Conversely, a positioning of baffle members 34 further from nozzle 22 can create a more uniform high-absorbency material concentration along the web cross-direction. This arrangement can produce an absorbent structure wherein the web side edges have approximately the same concentration of high-absorbency material as the web central region. Thus, by suitably adjusting the spacing between baffle members 34 and the location of the baffles along the machine direction of chamber 10, one can regulate the system to produce a desired, concentration variation or gradient measured from the central portion of web 41 to each of the web lateral side edges.

Baffles 34 can also be employed to produce a greater fiber concentration and basis weight in the medial portion 43 of web 41. As the baffles are slanted further from the vertical to extend further into the interior of chamber 10, there is a greater concentration of the fibers into the web medial portion. Web 41 can thus be selectively provided with a contoured, "humped" cross-sectional profile.

In the method and apparatus of the present invention, the arrangement and configuration of the conduit bend sections are important, because it is desirable to maintain a substantially uniform distribution of high-absorbency particles over the cross section of transport pipeline 56. Conventional conduit bend sections, however, have not been able to maintain the desired uniformity of the gas/particle dispersion 54, especially in those conduit regions where the particle dispersion is departing from a bend section.

In conventional bend sections, such as curved sections, ordinary T-bend sections, and induced "vortex" sections, the dispersed high-absorbency particles can become concentrated toward the "outside", generally convex portion of the conduit bend during the process of changing the flow direction of particle dispersion 54. The high-absorbency particles can also become concentrated to form segregated, swirling ribbons of particulate material within the general gas flow. These ribbons can spiral down the conduit pipeline, hugging against the conduit walls. This concentration of high-absorbency material into particular portions of the transport conduit is undesirable because it makes it difficult to regulate the distribution of the high-absorbency particles into the fibers being deposited onto forming layer 30. The segregated, swirling patterns of high-absorbency material can create a pulsating effect which can, in turn, produce an uneven flow distribution of high-absorbency particles entering chamber 10. This pulsating flow can create an uneven intermixing between the high-absorbency material and the absorbent fibers, and can produce undesired variations in the distribution patterns of high-absorbency material through the thickness and across the width of web 41.

To better direct the flow of particle dispersion 54 around bends, the present invention employs a distinctively configured direction-changing conduit section. As representatively shown in FIG. 6, this conduit section includes a first, substantially linear conduit section 82 and a second, substantially linear conduit section 84. The second linear section intersects in fluid communication with the first linear section to form a T-bend type intersection therewith. The T-bend has an entrance arm 86 into which the flow of particle dispersion 54 enters the fitting, an exit arm 88 from which the particle dispersion departs the fitting, and has a blind arm 90, which is ordinarily employed to reduce the erosion wear of the fitting.

Figure 6:
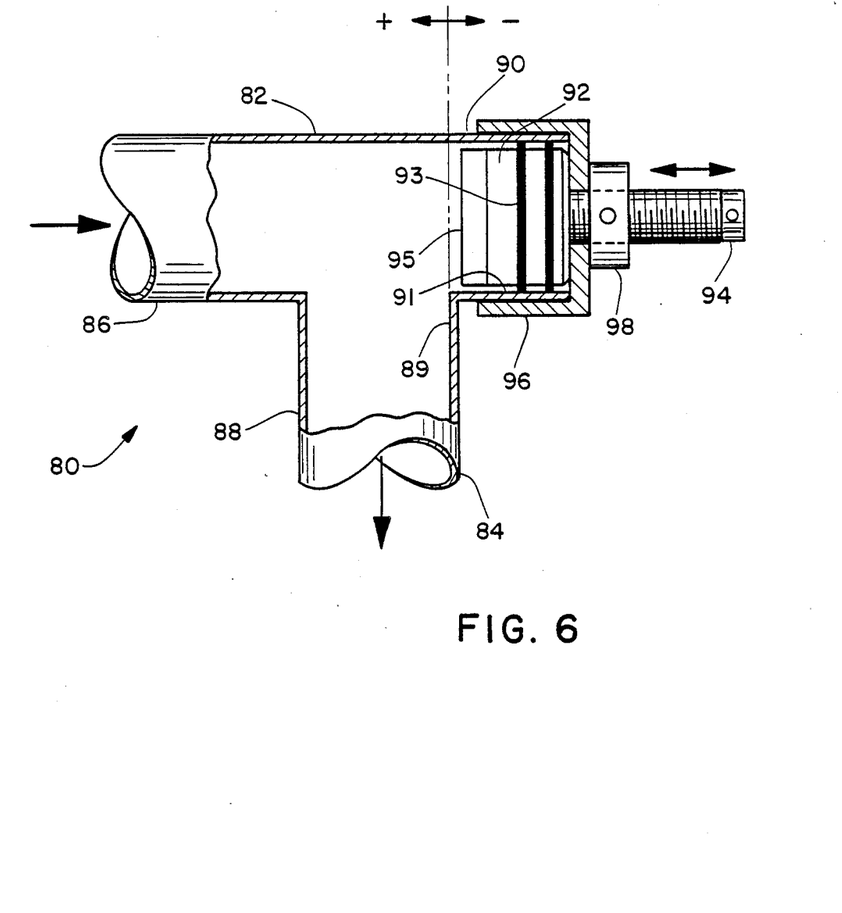
FIG. 6 representatively shows a partial, cross-sectional view of an adjustable, blinded T-bend fitting employed in the apparatus of the invention.

It has been found, however, that conventional conduit bend fittings, including conventional blinded T-bend fittings, have produced undesired segregations of the high-absorbency particles within the transporting gas. The undesired segregations can advantageously be reduced by employing adjustment means located in the blinded arm 90 of the T-bend. The adjustment means selectively controls the effective conduit length of the blinded arm of the T-bend.

In the embodiment shown in FIG. 6, the adjustment means comprises a plug member 92, which substantially conforms to the interior contour shape of blinded T-bend arm 90. Screw member 94 mounts on blinded arm 90 with mounting flange 96, and is connected to selectively move plug member 92 along the length dimension of blinded arm 90 upon the rotation of the screw member. In the shown embodiment, screw member 94 is constructed in a threaded engagement with a collar 98, which is connected and preferably affixed to mounting flange 96. Sealing means, such as gaskets 93 are seated in a side surface 91 of plug member 94 and contact the inside surface of blinded arm 90 to reduce the intrusion of particles into the region behind the plug member. Such an intrusion of particles could inhibit the adjustment movements of plug member 92 along blinded arm 90. Screw member 94 and plug member 92 are suitably sized and configured to move face surface 95 of the plug member to a location which is recessed into or protruding from blinded arm 90 by a selected distance. In a particular aspect of the invention, this adjustment distance ranges from about plus or minus 2.54 cm. relative to the nearest side wall 89 of exit arm 88.

While viewing into the flow conduit at or downstream from exit arm 88, for example with a sight window, the position of plug 92 can be suitably adjusted until one observes a substantially uniform distribution of high-absorbency particles within the transporting gas flow. The adjustment of plug member 92 operably disrupts the segregated particle flows and reestablishes the desired, substantially random intermixture of particles and gas.

Having thus described the invention in rather full detail, it will be readily apparent to a person having ordinary skill in the art that various changes and modifications can be made without departing from the spirit of the invention. All of such changes and modifications are contemplated as being within the scope of the present invention, as defined by the subjoined claims.

What is claimed is:

1. An apparatus for forming an absorbent body, comprising:
    a. a forming chamber;
    b. fiber delivering means for providing a flow of fibrous material within said forming chamber;
    c. a forming layer, which is located in said forming chamber and is movable therein, for receiving a deposit of said fibrous material thereon to form said absorbent body;

d. conduit means for supplying a flow of dispersed bodies of high-absorbency material, which enters said forming chamber and intermixes with said flow of fibrous material therein; and e. regulating means for controlling a velocity of said flow of high-absorbency material into said flow of fibrous material to provide high-absorbency material having various shorter, longer and intermediate trajectories, wherein said various trajectories deposit the high-absorbency material at different locations in said forming chamber to thereby selectively distribute said high-absorbency material through a thickness dimension of said absorbent body to produce a concentration gradient of high-absorbency material along said thickness dimension.

2. An apparatus as recited in claim 1, wherein said regulating means directs said flow of high-absorbency material along an initial flow direction which is oriented within about 45 degrees relative to a plane positioned generally parallel with said forming layer.

3. An apparatus as recited in claim 1, wherein said regulating means directs said flow high-absorbency material along an initial flow direction which is generally parallel with a movement direction of said forming layer.

4. An apparatus as recited in claim 1, wherein said regulating means provides an initial flow of said high-absorbency material into said forming chamber at a speed which ranges from about 15-45 m/sec.

5. An apparatus as recited in claim 1 wherein said regulating means includes one or more baffle members for controlling a lateral, cross-directional distribution of said high-absorbency material within the fibrous material deposited on said forming layer.

6. An apparatus as recited in claim 5, wherein said baffle members have substantially vertically disposed major surfaces which are oriented substantially parallel with a movement direction of said forming layer.

7. An apparatus as recited in claim 5, wherein said baffle members are moveable along said movement direction of said forming layer.

8. An apparatus as recited in claim 1, wherein said conduit means includes guiding means for maintaining a substantially uniform, cross-sectional distribution of high-absorbency bodies within a fluid flow through said conduit means.

9. An apparatus as recited in claim 8, wherein said guiding means includes a conduit section for changing a flow direction of a gas/particle dispersion, comprising:

a. a first, substantially linear conduit section;

b. a second, substantially linear conduit section which intersects in fluid communication with said first conduit section to form a T-bend therewith, said T-bend including an entrance arm into which said dispersion enters said conduit section, an exit arm from which said dispersion departs from said intersection with a changed flow direction, and a blended arm; and c. adjustment means located in said blinded arm for selectively controlling an effective conduit length of said blinded arm to thereby disrupt segregated particle flows and provide a substantially uniform distribution of said particles in said gas flow from said exit arm.

10. An apparatus as recited in claim 1, wherein said regulating means controls a flow speed of said high-absorbency material along a movement direction of said forming layer, and adjusts an angular orientation of said conduit means relative to a plane positioned generally parallel to said forming layer to adjust said trajectories.

11. A method for forming an absorbent body, comprising the steps of:

a. providing a flow of fibrous material with a forming chamber;

b. depositing said fibrous material onto a forming layer, which is located in said forming chamber and is moveable therein, to form said absorbent body;

c. supplying a flow of dispersed bodies of high-absorbency material, which enters said forming chamber and intermixes with said flow of fibrous material therein; and d. controlling a flow velocity of said high-absorbency material into said flow of fibrous material to provide high-absorbency material having various shorter, longer and intermediate trajectories, wherein said various trajectories deposit the high-absorbency material at different locations in said forming chamber to thereby selectively distribute said absorbent body to produce a concentration gradient of high-absorbency material along said thickness dimension.

12. A method as recited in claim 11, wherein said flow of high-absorbency material is directed along an initial flow direction which is oriented with about 45 degrees relative to a plane positioned generally parallel with am movement direction of said forming layer.

13. A method as recited in claim 11, wherein said flow of high-absorbency material is directed along an initial flow direction which is generally parallel with a movement direction of said forming layer.

14. A method as recited in claim 11, wherein a lateral, cross-directional distribution of said high-absorbency material within the fibrous material deposited on said forming layer is controlled with one or more baffle members 15. A method as recited in claim 14, wherein said baffle members have substantially vertically disposed major surfaces which are oriented substantially parallel with a movement direction of said forming layer.

16. A method as recited in claim 14, wherein said baffle members are moveable along said movement direction of said forming layer 17. A method as recited in claim 14, wherein said supplying step (c) includes maintaining a substantially uniform, cross-sectional distribution of high-absorbency bodies within a fluid flow.

18. A method as recited in claim 11, wherein said controlling step (d) controls a flow speed of said high-absorbency material along a movement direction of said forming layer and adjusts an angular orientation of said supplied flow of high-absorbency material relative to a plane positioned generally parallel to said forming layer to adjust said trajectories.

19. A conduit section for changing a flow direction of a gas/particle dispersion, comprising:

a. a first, substantially linear conduit section;

b. a second, substantially linear conduit section which intersects in fluid communication with said first conduit section to form a T-bend enters said conduit section, an exit arm from which said dispersion departs from said intersection with a changed flow direction, and a blinded arm; and c. adjustment means for selectively controlling an effective conduit length of said blinded arm, said adjustment means located in said blinded on and constructed to position a face surface of said adjustment means at a location which can be recessed into and protruded from said blinded arm by a selected distance to thereby provide a substantially uniform distribution of particles in said dispersion departing from said exit arm.

20. A conduit section as recited in claim 19, wherein said adjustment means comprises:
   a plug member which substantially conforms to an interior contour of said blinded T-bend arm, and
   an adjustment member which is connected to move said plug member along said blinded T-bend arm to position a face surface of said plug member at a location which can be recessed into and protruded from said blinded T-bend arm by a selected distance.

21. A conduit section as recited in claim 19, wherein said face surface can be recessed into or protruded from said blinded arm by a distance range of about 2.54 cm.

22. A conduit section as recited in claim 20, wherein said face surface can be recessed into or protruded from said blinded arm by a distance range of about 2.54 cm.

23. A conduit section as recited in claim 20, further comprising sealing means for reducing an intrusion of particles into a region behind said plug member, which intrusion could inhibit control movements of said plug member.

24. A conduit section as recited in claim 20 wherein said adjustment member comprises a screw member which is mounted on said blinded arm and is connected to move said plug member along said blinded arm upon rotating said screw member.

25. A conduit section for changing a flow direction of a gas/particle dispersion, comprising:
   a. a first, substantially linear conduit section;
   b. a second, substantially linear conduit section which intersects in fluid communication with said first conduit section to form a T-bend therewith, said T-bend including an entrance arm into which said dispersion enters said conduit section, an exit arm from which said dispersion departs from said intersections with a changed flow direction, and a blinded arm;
   c. adjustment means for selectively controlling an effective conduit length of said blinded arm to provide a substantially uniform distribution of particles in said dispersion departing from said exit arm; and
   d. sealing means for reducing an intrusion of particles into a blinded arm region behind said adjustment means, which intrusion could inhibit control movements of a face surface of said adjustment means.

* * * * *